(12) United States Patent
Eischen et al.

(10) Patent No.: US 8,295,923 B2
(45) Date of Patent: Oct. 23, 2012

(54) SACRIFICIAL ELECTRODE DESIGN AND DELIVERY SPECIES SUITABLE FOR PROLONGED IONTOPHORESIS APPLICATION PERIODS

(75) Inventors: Kathleen A. Eischen, St. Paul, MN (US); Carter R. Anderson, Inver Grove Heights, MN (US); Russell L. Morris, Lindstrom, MN (US)

(73) Assignee: Teikoku Pharma USA, Inc., San Jose, CA (US)

( * ) Notice: Subject to any disclaimer, the term of this patent is extended or adjusted under 35 U.S.C. 154(b) by 2 days.

(21) Appl. No.: 12/597,941

(22) PCT Filed: Aug. 31, 2009

(86) PCT No.: PCT/US2009/004928
§ 371 (c)(1),
(2), (4) Date: Oct. 28, 2009

(87) PCT Pub. No.: WO2010/027444
PCT Pub. Date: Mar. 11, 2010

(65) Prior Publication Data
US 2011/0245755 A1  Oct. 6, 2011

Related U.S. Application Data

(60) Provisional application No. 61/093,464, filed on Sep. 2, 2008.

(51) Int. Cl.
*A61N 1/30* (2006.01)
(52) U.S. Cl. .......................................... 604/20; 604/501
(58) Field of Classification Search .................... 604/20, 604/501; 424/618
See application file for complete search history.

(56) References Cited

U.S. PATENT DOCUMENTS

| | | | |
|---|---|---|---|
| 4,744,787 A | 5/1988 | Phipps et al. | |
| 5,503,632 A | 4/1996 | Haak | |
| 6,289,241 B1 * | 9/2001 | Phipps | 604/20 |
| 6,546,282 B1 * | 4/2003 | Inoue et al. | 604/20 |
| 6,597,947 B1 * | 7/2003 | Inoue et al. | 604/20 |
| 6,731,977 B2 | 5/2004 | Beck | |
| 6,745,071 B1 | 6/2004 | Anderson et al. | |
| 6,858,018 B1 * | 2/2005 | Green et al. | 604/19 |
| 7,031,769 B2 * | 4/2006 | Anderson et al. | 604/20 |

(Continued)

OTHER PUBLICATIONS

Notification Concerning Transmittal of International Preliminary Report on Patentability (Chapter 1 of the Patent Cooperation Treaty) with International Preliminary Report on Patentability dated Mar. 17, 2011 from the International Bureau of WIPO, 8 pages.

(Continued)

*Primary Examiner* — Kevin C Sirmons
*Assistant Examiner* — Michael J Anderson
(74) *Attorney, Agent, or Firm* — Bozicevic, Field & Francis LLP; Bret E. Field

(57) ABSTRACT

A wearable iontophoresis device for the prolonged delivery of a positively charged pharmaceutical species from a salt formulation is disclosed that includes a readily oxidizable metal-based sacrificial anode in the form of a generally planar layer having a connecting area that has a width that is sufficient to insure complete consumption of the oxidizable metal wherein the anode is configured to have a minimum operating life of at least 6 hours under skin-safe conditions, and a drug delivery gel pad in electrical contact with said anode for accommodating a gel containing a positively charged pharmaceutical species in salt form formulated for transdermal delivery.

47 Claims, 6 Drawing Sheets

U.S. PATENT DOCUMENTS

| | | |
|---|---|---|
| 7,031,796 B2 | 4/2006 | Lange |
| 2003/0212397 A1* | 11/2003 | Avrahami et al. ............... 606/41 |
| 2004/0049147 A1* | 3/2004 | Edel et al. ...................... 604/20 |
| 2004/0167460 A1* | 8/2004 | Anderson et al. ............... 604/20 |
| 2005/0131336 A1* | 6/2005 | Mori et al. ..................... 604/20 |
| 2005/0171464 A1* | 8/2005 | Phipps et al. ................... 604/20 |
| 2005/0228335 A1* | 10/2005 | Reddy et al. ................... 604/20 |
| 2006/0161132 A1* | 7/2006 | Anderson et al. ............. 604/501 |
| 2006/0184093 A1 | 8/2006 | Phipps et al. |
| 2006/0275352 A1* | 12/2006 | Southam et al. ............. 424/448 |
| 2007/0083186 A1* | 4/2007 | Carter et al. .................. 604/501 |
| 2008/0009782 A1* | 1/2008 | Gale et al. ...................... 604/20 |
| 2008/0058700 A1* | 3/2008 | Hause et al. .................... 604/20 |
| 2008/0114284 A1 | 5/2008 | Anderson et al. |
| 2008/0154230 A1* | 6/2008 | Subramony et al. .......... 604/501 |

OTHER PUBLICATIONS

International Search Report and Written Opinion dated Oct. 16, 2009.

* cited by examiner

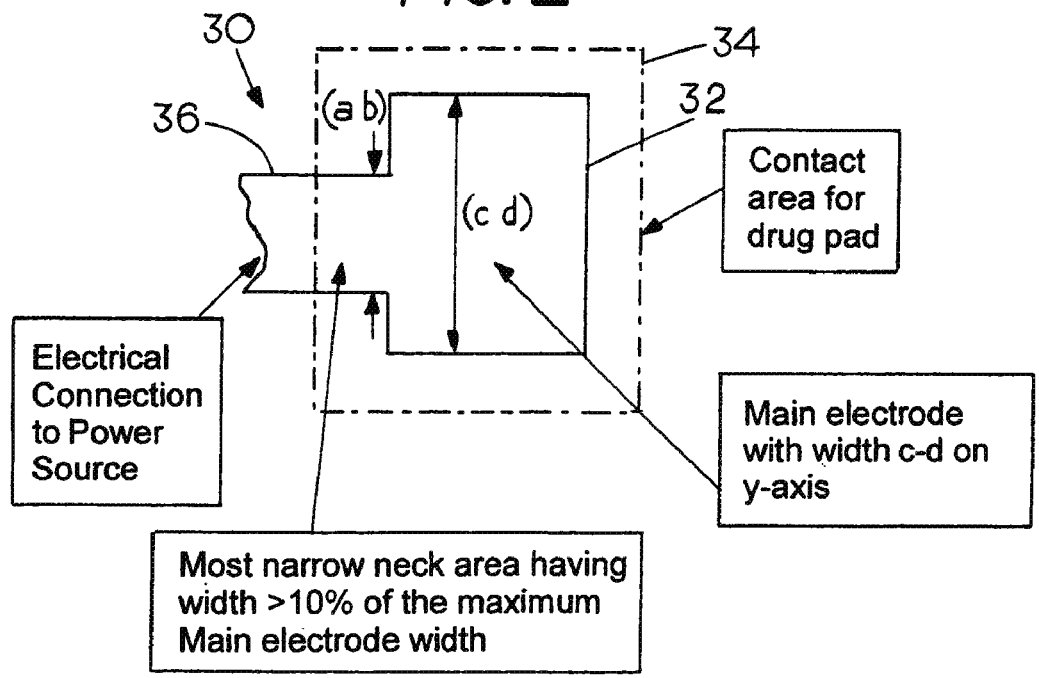
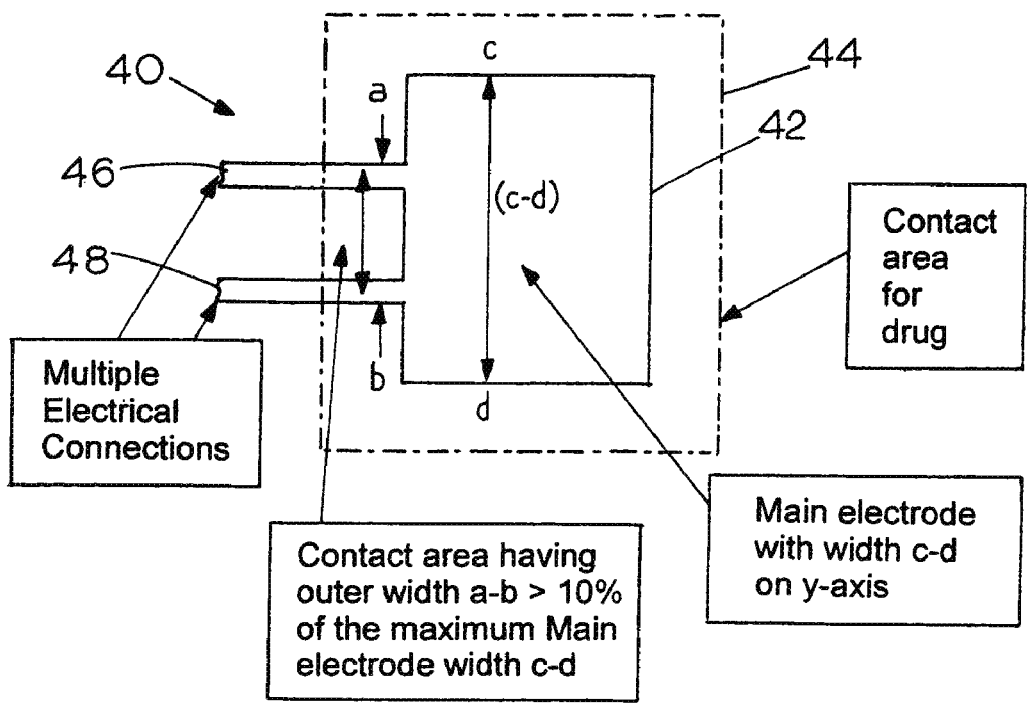

SACRIFICIAL ELECTRODE DESIGN AND DELIVERY SPECIES SUITABLE FOR PROLONGED IONTOPHORESIS APPLICATION PERIODS

CROSS-REFERENCED TO RELATED APPLICATIONS

This application is a non-provisional application of Application No. 61/093,464, filed Sep. 2, 2008 and claims priority from that application which is also deemed incorporated by reference in its entirety in this application.

BACKGROUND OF THE INVENTION

I. Field of the Invention

The present invention relates generally to a system for transdermal delivery of therapeutic agents using skin-worn iontophoresis devices to introduce such substances into the body. More specifically, this invention provides a method for safe prolonged delivery of drugs that are formulated as hydrochloride salts, particularly including those which are normally skin irritants, such as donepezil HCl, using a skin-worn patch including a sacrificial active metal based electrode system.

II. Related Art

The process of iontophoresis has found commercial use in the delivery of many ionically charged therapeutic agent compounds. In this delivery method, ions bearing a charge are driven across the skin at the site of an electrode of like charge. The application time and level of current flow (usually reported in units of milli-amp minutes) directly correlates to the amount of drug delivered, and the efficiency of drug delivery can be measured by the proportion of current carried by drug molecules, relative to the current carried by competing non-medication ions having the same charge as the medication.

Self-contained, wearable iontophoretic systems have been developed in which the electrical circuitry and power supply have been integrated into a single, skin-worn patch that includes a pair of electrodes in electrical communication with a subject's skin. An important consideration for reliability and function of iontophoretic devices rests in the choice and design of the electrodes used. Electrode materials can be "inert", remaining unchanged during the passage of current. Examples include platinum, gold, and carbon. Inert electrode materials, however, are associated with the possibility of pH changes at the electrode sites as a result of electrochemical oxidation of water at the anode and reduction of water at the cathode. These reactions occur with current flow and produce acidic changes at the anode and alkaline changes at the cathode which can cause moderate or even severe skin irritation or burns with a skin-worn patch.

The pH changes associated with inert electrode materials can be eliminated by the use of a "sacrificial" electrode materials which are materials that are consumed by an electrochemical reaction during the passage of current. For example, silver chloride in cathodes is reduced to silver during the passage of current. Conversely, sacrificial anodes are oxidized and include materials such as silver, zinc, or other readily oxidizable metals (metals that oxidize in preference to water).

In iontophoresis devices, the sacrificial material content must be at least sufficient to deliver the intended amount of drug and to last for the intended delivery period. To accomplish this, it is desirable that the electrode be designed to continue to function until the sacrificial material of the electrode is completely depleted avoiding any premature break in electrical connection to the electrode during a prolonged delivery period.

Another important factor for consideration with iontophoresis for prolonged delivery periods relates to skin irritation. Compounds that are themselves irritants to skin have heretofore not been suitable for delivery using iontophoretic devices, as these devices require skin contact with these compounds. This is particularly significant in applications designed to deliver such compounds into the skin for prolonged periods (periods of at least 6 hours and up to 7 days or more, for example).

SUMMARY OF THE INVENTION

By means of the present development, successful prolonged skin-safe and effective transdermal delivery of a variety of therapeutic substances, including analgesics, antiemetics and including therapeutic substances which are themselves moderate to severe skin irritants, can now be accomplished using iontophoresis. Certain compounds in a compatible salt form can be formulated into water-based hydrogels at a concentration generally of about 10% or less and can be successfully and safely delivered transdermally using iontophoresis devices. The iontophoresis devices include a sacrificial electrode of a readily oxidizable metal in a skin-worn patch operable at very low current densities, generally less than 100 $\mu A/cm^2$. Patches in accordance with the invention can deliver such compounds into the skin for periods of at least 6 hours and up to 7 days or more in a generally stable pH environment.

Embodiments provide iontophoretic patch devices that are safely wearable for a prolonged period and dedicated to the delivery of a positively charged compound that may be formulated as a hydrochloride salt contained in a water-based (aqueous) hydrogel. Example patches include a sacrificial anode containing an amount of readily oxidizable metal such as silver which is designed to be consumed over a prolonged period. These patches further include a source of electric current which can be controlled at a low output, skin-safe level.

A particular exemplary embodiment provides a single-use wearable iontophoretic patch dedicated to the delivery of donepezil HCl, a pharmaceutical well known as a skin irritant. In the patch, an amount of the drug is incorporated in an aqueous hydrogel carried by an absorbent delivery gel pad. The patch includes a silver-containing anode and a silver chloride cathode and is further configured to deliver the drug using a current density<100 $\mu A/cm^2$ for a period of up to 7 days.

An important aspect of the invention has to do with electrode and connecting conductor construction. Accordingly, electrodes, particularly anodes have been devised in which the sacrificial material is entirely consumed during the prolonged operation of the iontophoresis devices. It has been found that in order to assure complete consumption of the sacrificial electrode material and eliminate premature electrode failure caused by a premature severing of the connector segment, a sacrificial anode configured as a continuous layer needs a connecting conductor segment or neck segment generally ≧5% of the corresponding maximum width dimension of the anode and, preferably, the connecting conductor segment is ≧10% of the corresponding maximum width. The anode further should contain sufficient sacrificial silver or other readily oxidizable metal to deliver the required amount of therapeutic agent over the required time span before it is consumed. The metal may be a layer applied as by a silk screening process, or the like, and the thickness of the metal layer may vary, but is generally from about 0.0002 inch (5 microns) to about 0.002 inch (50 microns).

In certain embodiments, the anode layer is applied on top of a gel-absorbing drug delivery pad designed to contain a hydrogel formulated with the positively charged hydrochloride salt to be administered. The anode area is adapted to receive the gel-absorbing drug delivery pad containing hydrochloride salt to be administered. The anode area needs to encompass the area contacted by the agent for all of the agent to be administered. Preferably, the gel pad surface to which the silver is applied is irregular or rough or otherwise configured to increase the effective electrode area and create a relatively high surface area that is greater than the surface area of a corresponding smooth surfaced electrode of equal dimensional area. This construction also reduces contact resistance between electrode and gel.

As indicated, it has been found that using the electrode system of the present invention iontophoresis can be performed in a manner which is skin-safe and effective even for the delivery of known skin-irritating agents including donepezil HCl. As indicated, it has also been found that clinically effective doses of this agent can be administered for up to seven days without adverse skin symptoms in the great majority of cases.

BRIEF DESCRIPTION OF THE DRAWINGS

In the drawings wherein like characters denote like parts throughout the same:

FIG. 2 is a schematic representation of an anode design in accordance with the present invention utilizing a extended interconnect zone;

FIG. 3 is a representation of an alternate anode design in accordance with the present invention utilizing multiple electrical connections;

FIG. 6B depicts a schematic representation of an example circuit suitable for the patch of FIG. 6a;

DETAILED DESCRIPTION

Figure 1A:
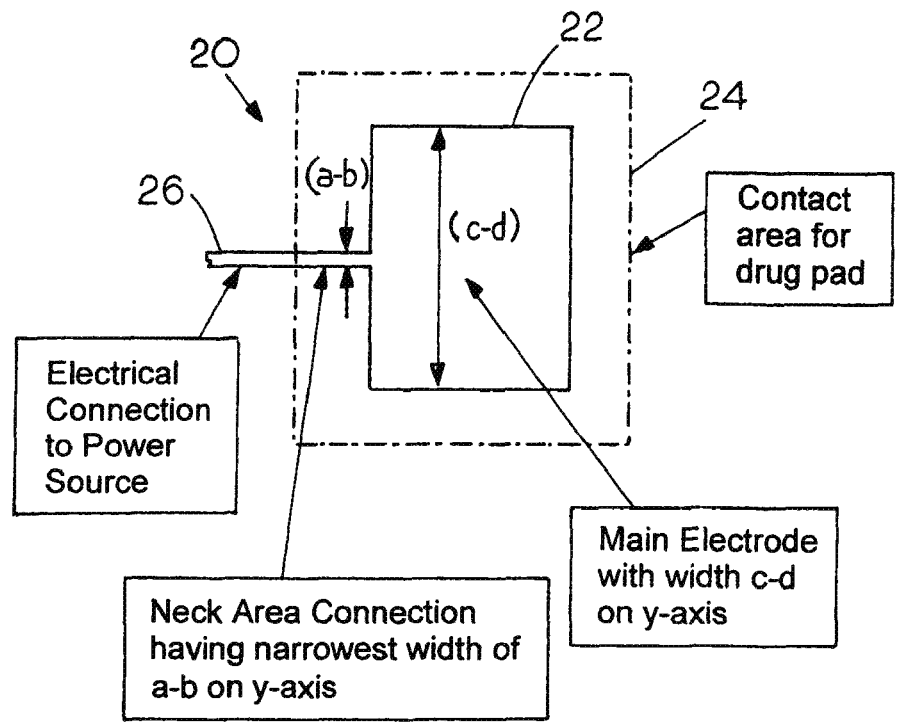
FIGS. 1A and 1B depict schematic representations of a typical prior art sacrificial silver anode configuration, prone to premature failure, a failure mode being illustrated in FIG. 1B.
Figure 1B:
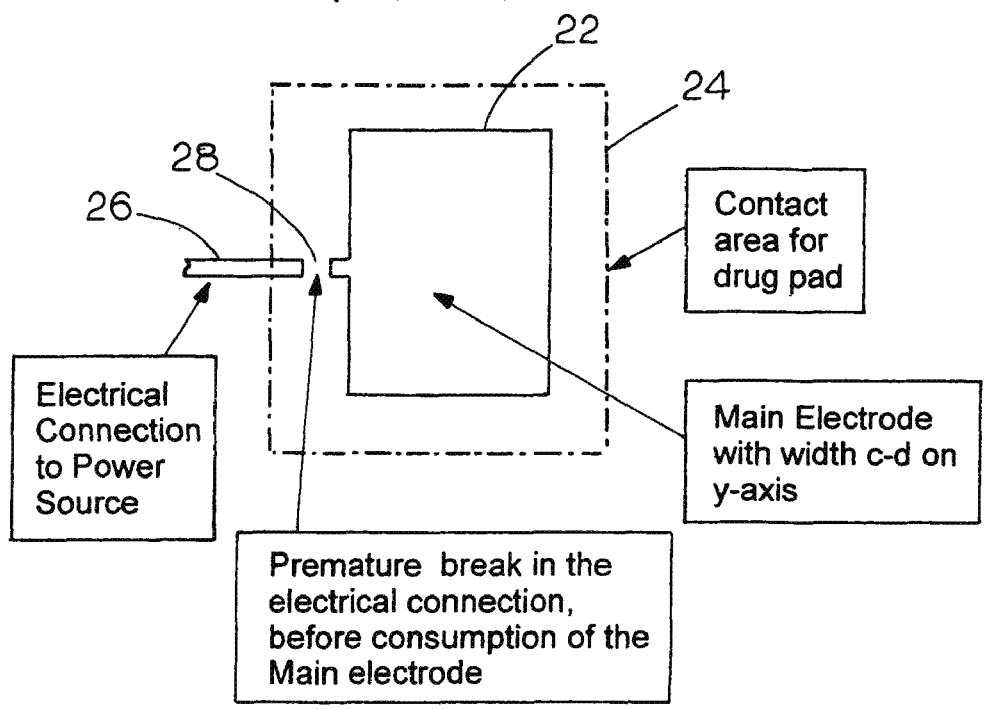

The invention pertains to a method for treating a subject transdermally with a variety of therapeutic substances, particularly drugs that are normally skin irritants, that can safely be administered in the form of a salt using a skin-worn iontophoresis patch. By means of the present invention, for example, it has been found that an effective amount of donepezil can be transdermally administered to a subject over a prolonged period without substantially irritating the subject's skin. Donepezil is known to be a skin irritating agent. The Material Safety Data Sheet (MSDS) for this compound warns that it is harmful if held in contact with skin.

The invention pertains, in an aspect, to an integrated iontophoretic transdermal patch for the prolonged delivery of a positively charged drug in a salt, preferably a hydrochloride salt, form. The patch is particularly useful for long term delivery of agents exemplified by donepezil and other agents that are normally skin irritants. Further, the electrode to be used in the iontophoretic patch comprises an amount of sacrificial metal, preferably silver, and preferentially is generally planar in form and applied, for example, by a screen-printing process.

Sacrificial anodes containing silver have been found to be particularly useful for delivery of therapeutic agents or drugs that are present as hydrochloride (HCl) salts. As silver is oxidized, silver ions ($Ag+$) produced combine with chloride ions ($Cl-$) of the drug to form insoluble silver chloride (AgCl). The reaction does not interfere with further silver metal oxidation and also reduces generation of competing ions (ions similarly charged to the drug), the existence which can reduce the efficiency of drug delivery.

DEFINITIONS

1. The term "electrode" or "anode", as used herein, is defined as the portion of the readily oxidizable metal such as silver in the iontophoretic patch that is in contact with a positively charged drug solution.

2. As used herein, the terms "neck area" or "neck connecting segment" of the electrode or anode is the narrowest region of the electrode in contact with the drug solution. Typically, the neck area is at an edge of the drug reservoir closest to the power source and provides electrical contact to the power source in the circuit.

3. The term "prolonged delivery" is defined as a sustained delivery of medication from the iontophoresis patch for a period of at least 6 hours, and as long as 7 days or more.

4. The terms "skin-safe" and "does not substantially irritate a subject's skin" as used herein are meant to include patches, the operation of which result in a skin erythema score of 2.50 or less, preferably 2.00 or less, or, or most preferably, 1.00 or less about two hours after patch removal. In this scoring system, 0=no erythema, 1=very slight erythema (barely perceptible), 2=well defined erythema, 3=moderate to severe erythema, 4=sever erythema to slight eschar formation.

Electrodes

In relation to this invention, we have also discovered that certain designs or constructions of sacrificial anodes provide superior protection against premature failure, i.e., failure of the electrode due to a premature breach in electrical connection to the electrode before depletion of the sacrificial metal material in the electrode area. Accordingly, it has been found that if the neck area of the planar electrode is of a width generally 5% or more of the maximum electrode width, in either the x or y direction, or as much as fully enveloping the electrode, the conductor arc is sufficient so that the electrode will be reliable in operation for the full prolonged delivery period calculated for depletion of sacrificial metal.

To minimize waste of sacrificial metal such as silver and also to minimize contact resistance of the electrode to the drug reservoir an optimized surface has been found. The optimum surface has been discovered to be a rough surface contour, where the difference between high and low points of the electrode surface is 25% or more of the total electrode surface. By using a rough surface contour, the effective contact surface area between sacrificial metal and the drug can be increased by 50% or more as compared to the area based on the corresponding flat surface. This rough surface contour electrode may also be viewed as a high-surface area electrode, where the actual surface area of the electrode exceeds the surface area of a corresponding virtual electrode that is defined by the same length and width dimensions of the high surface area electrode.

FIGS. 1A-5B illustrate representative prior art and present concept sacrificial anode designs. FIG. 1A depicts a schematic representation of a typical prior art sacrificial silver anode configuration generally at 20 which includes a main electrode 22 situated in a contact area for a drug pad at 24. The main electrode 22 is shown with a width on the vertical or y axis of (c-d) and a neck area defined as (a-b) which represents the narrowest part of an electrical connection 26 which connects the electrode 22 with a corresponding power source. The neck area (a-b) also represents the narrowest width on the y or vertical axis. With prior anodes, it has been found that typically the width (a-b)<5% of the width (c-d). As shown in the schematic drawing of FIG. 1B, the narrowness or lack of sufficient connective area with regard to the connection 26 often results in a premature break in the electrical connection prior to the consumption of the main or sacrificial electrode material. Such a break is shown at 28.

FIG. 2, on the other hand, illustrates a schematic representation of an anode design in accordance with the present invention, generally at 30, which includes a main electrode 32 situated in a contact area for a drug pad in phantom at 34 and which has a large area electrical connection to a power source or neck area at 36. This figure illustrates an electrode configuration in which (a-b)>10% of (c-d).

FIG. 3 shows an alternate embodiment of the sacrificial electrode of the invention generally at 40 which includes a main electrode 42 situated in a contact area for a drug pad at 44 and which is provided with multiple electrical connections to a power source shown as a pair of connections at 46 and 48. This embodiment has a combined neck area width (a-b) which is also >10% of the maximum width of the main electrode of the electrode shown at (c-d).

In the embodiments illustrated in FIGS. 2 and 3, the contact area of the drug pad exceeds the area of the main electrode. As such, in these embodiments, none of the main electrode extends outside of the contact area for the drug pad, and therefore the "neck area" is defined solely by the one or more electrical connections that extend from the main electrode beyond the contact area for the drug.

Figure 4A:
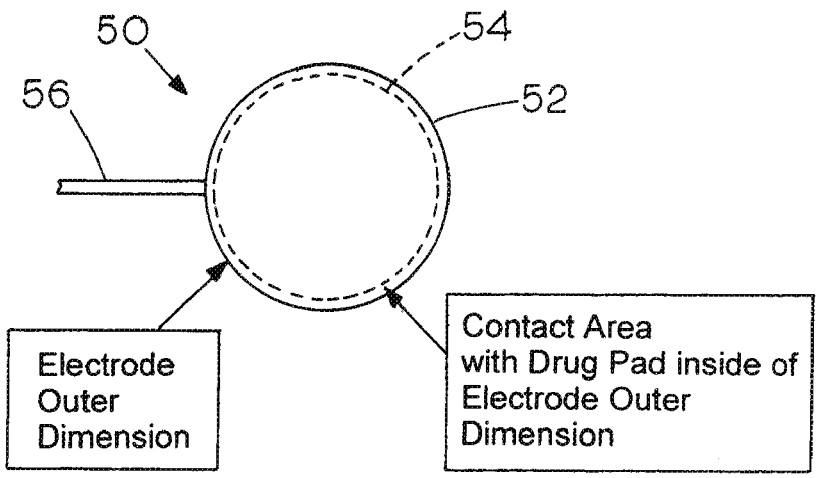
FIGS. 4A and 4B are representations of other anode designs utilizing rectangular and circular shapes.

A further embodiment is shown in FIG. 4A at 50 in which the main electrode is shown as a circular device at 52 which exceeds the width or extends outside of the drug pad area shown in phantom at 54. As such, in contrast to the embodiments shown in FIGS. 2 and 3, the main electrode extends outside of the contact area for the drug pad and an example of embodiments where at least a portion of the main electrode extends beyond the area defined by the drug pad. In the embodiment shown in FIG. 4A, because a portion of the main electrode extends beyond the area defined by the drug pad, the neck area encompasses the electrode. An electrical connection is shown at 56. As such, the neck area in the embodiment illustrated in FIG. 4A includes both the electrical connection and that portion of the main electrode that extends beyond the area defined by the drug pad.

Figure 4B:
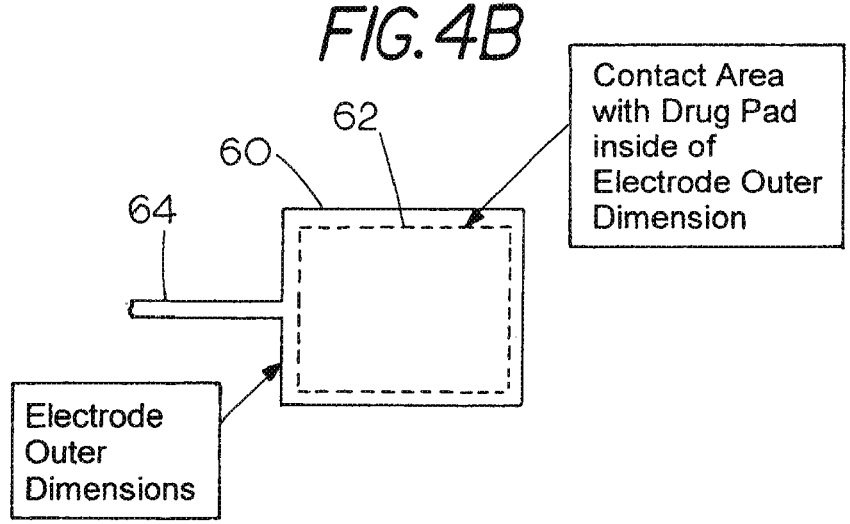

FIG. 4B depicts a main electrode in a rectangular shape 60 that also exceeds the drug pad area shown in phantom at 62 with electrical connection 64. As with FIG. 4A, the neck area in the embodiment illustrated in FIG. 4B includes both the electrical connection and that portion of the main electrode that extends beyond the area defined by the drug pad.

With respect to the embodiments of FIGS. 4A and 4B, these are examples of device configurations in which the main electrode has an area that exceeds the contact area of the drug pad, where in some instances the area of the main electrode may exceed the area of the drug pad by 5% or more, such as 10% or more, including 15% or more. Depending on a given desired configuration, the main electrode may extend beyond all sides of the drug pad or only some of the sides of the drug pad.

Figure 5A:
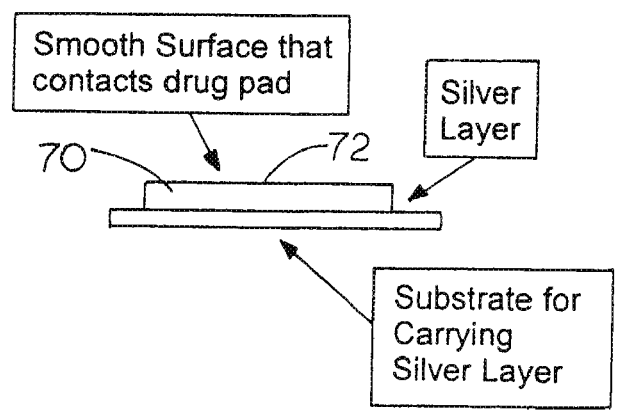
FIGS. 5A and 5B are schematic cross sectional depictions of a metal anode layer showing conventional and preferred topography.

FIG. 5A is a schematic of a sacrificial anode electrode layer 70 laid down as a smooth surface 72 or a substrate layer 74 which produces an electrode area equal to the area of the smooth surface.

Figure 5B:
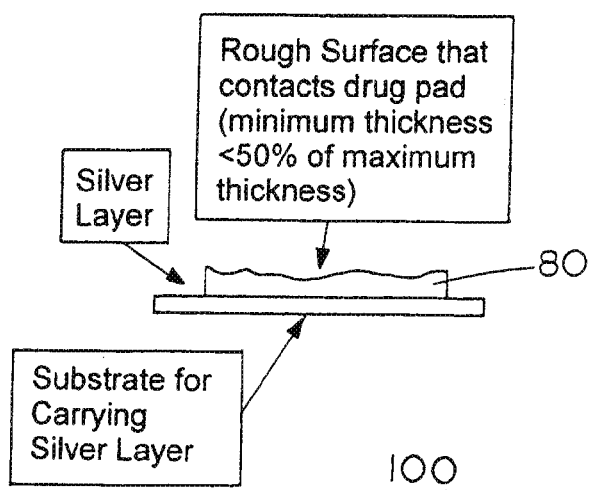

FIG. 5B illustrates a sacrificial anode layer 80 having a rough surface at 82 which may correspond to the rough surface afforded by a drug pad in which the electrode may be laid down such that the minimum thickness of material covering the drug pad is 50% or less of the maximum thickness. In any event, however, it is apparent that utilizing a rough surface will significantly increase the effective surface area of the electrode and create a relatively high area of reactive material that is greater than the area occupied by the electrode as determined by length and width dimensions. This enables placement of a larger amount of consumable electrode material in a smaller area and also enlarges the contact area between the drug pad containing the drug and the electrode thereby reducing the contact resistance between a formulated drug material and the electrode. Such a construction may increase the contact area by 50 to 100% based on the electrode footprint. The embodiment illustrated in FIG. 5B provides an example of a high surface area electrode.

It should be noted that in certain embodiments of the invention, a neck area as described above may be present but a high surface area electrode may not be present. In yet other embodiments, a neck area as described above may not be present but a high surface area electrode may be present. In still other embodiments, both a neck area as described above and a high surface area electrode may be present.

Skin-Worn Patches

The patches of the invention are preferably self-contained with respect to delivery of a substance of interest as a hydrochloride salt formulated in an aqueous hydrogel form suitable for transdermal administration. The patches deliver the compounds using iontophoresis and, more preferably, are complete integrated or combined devices which need only be removed from packaging and applied to the skin of a patient or subject or which require only simple assembly prior to being applied to the skin. Application of the patch to the skin completes the electrical iontophoresis circuit and the device begins transdermal administration of the therapeutic compound immediately. Preferably, the duration of time necessary to reach a clinically effective level is no more than about 6 hours and that level can be maintained for 7 days or more.

Figure 6A:
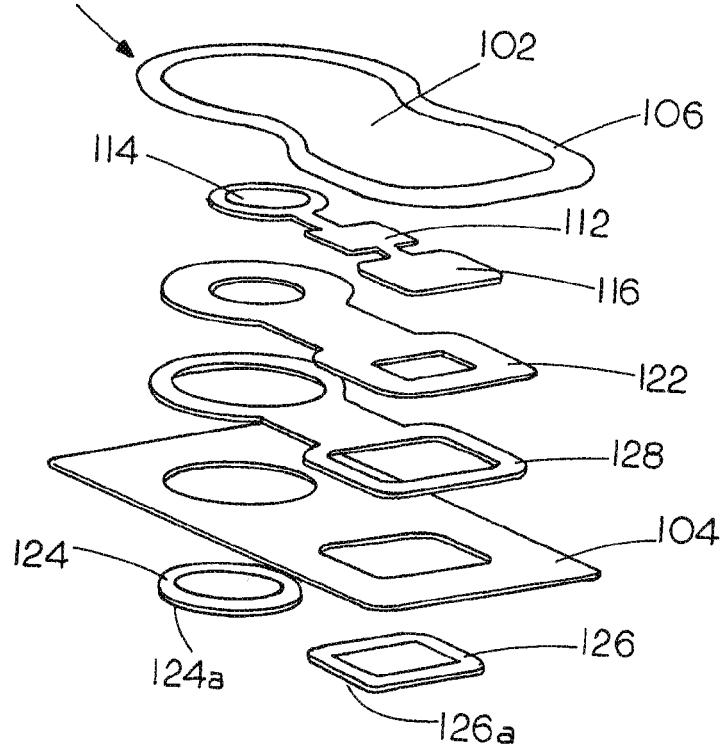
FIG. 6A depicts an exploded view of an iontophoretic patch construction suitable for use with the invention.

One embodiment of a patch suitable for delivery of donepezil HCl or other drug substance in accordance with the invention is shown generally at 100 in the exploded view of FIG. 6A and includes an impervious, non-conducting flexible backing layer 102 which is the upper or top layer in an applied patch and which may be attached to a peelable release layer 104. Backing layer 102 has a peripheral adhesive pattern of medical grade adhesive material applied to the inner or lower surface beneath the release layer (shown outlined at 106). The adhesive should be one suitable for a relatively long term adhesion to the skin of a patient or subject in a manner which also seals the periphery of the patch and prevents leakage of any materials beyond the adhesive border. Such materials are readily available articles of commerce.

Figure 6B:
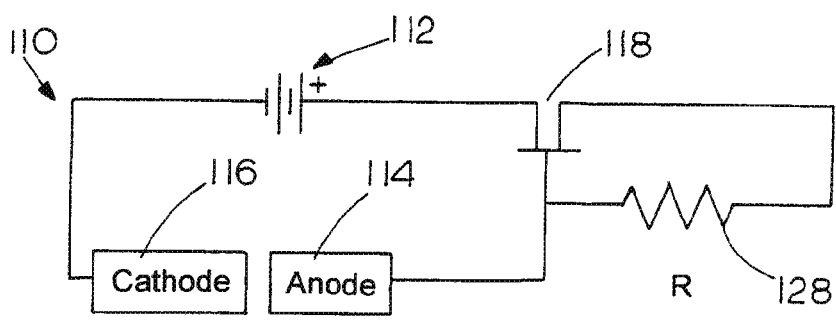

The patch further includes an electrical circuit assembly 110 which includes a power source which may be in the form of a pair of series connected lithium cells 112, a screen-printed silver anode 114, silver-silver chloride screen-printed cathode electrode 116. As shown in the schematic diagram of FIG. 6B, the circuit may also contain a series connected transistor and a resistor shown at 120 to provide output current level control. The circuit shown is completed by application to the skin and represents an example of a configuration that can be used to operate an iontophoresis patch and provide current level control. Such circuits are generally known and many applicable variations will occur to those skilled in the art. In some instances, the circuit is configured to provide the delivery currents described above.

A layer of double-sided medical grade tape 122 is included to provide internal adhesion of components of the device in an assembled state including adhesion between the peelable backing layer 102 and the electrical circuit assembly 110, absorbent pads 124 and 126 and the electrodes 114 and 116 and a shaped medical grade foamed tape member 128 which defines recesses designed to contain absorbent pads 124 and 126.

One of the absorbent gel-containing pads 124, 126 is associated with and in electrical communication with each electrode. One gel pad is used for containing or retaining the therapeutic compound of interest to be administered and a corresponding conductive material is contained in the other gel pad to enable the circuit to be completed at the time the patch is applied to the skin.

It should be noted that whether the pad containing material to be administered is associated with the anode or the cathode depends on the charge of the material itself. Accordingly, the hydrochloride or other salt materials administered in accordance with the examples of the present invention are positively charged and so are administered from the pad 124 associated with the anode 114 and the cathode pad 126 is imbibed with unmedicated conductive gel material. As indicated, recesses in the patch for receiving and containing the absorbent gel pads are provided as by a shaped foam barrier 128, as shown in the figure.

The anode and cathode pad structures are preferably of a non-woven material to maintain the continuity of drug-containing hydrogel material in the structure and may include a plurality of layers, possibly up to three layers, of material. Examples of materials that may be suitable for the absorbent non-woven matrix include cotton, polypropylene, polyethylene, and polyester. Most preferably, the absorbent material is polypropylene. One example of an embodiment includes a thick needle-punched polypropylene layer, a thin, permeable polyethylene net layer, and a thin, occlusive peripheral polypropylene layer as at 124a and 126a in FIG. 6A. The layers may be heat fused together without requiring adhesives. All three layers are cut to have the same outside perimeter shape. The occlusive layer 124a, 126a is cut to the shape of a perimeter ring that remains intact and occlusive. Inside the ring, the occlusive layer 124a, 126a is cut out completely or perforated so that the inside region becomes permeable. The permeable region is shaped to coincide with the shape of the anode 114 and cathode 116 electrodes, by allowing the gel to migrate through this layer and contact the full area of the electrodes when the device is assembled for use.

Importantly, the occlusive rings 124a and 126a provide a barrier for gel migration so the outside surface remains relatively dry during storage if the pads are separately stored and may be designed for adhesive attachment of the pad 124, 126 to a corresponding electrode recess using adhesive material in the rings during activation of the device.

The gels are preferably formulated with a viscosity range preferably between 8,000-120,000 centipoise, but this is not limited so long as the gel retains shape to be successfully assembled in the patch. The gels useful in the system may be formulated by dissolving an appropriate amount of formulated drug in a cross-linked or cross-linkable gelling agent such as HPMC (hydroxpropylmethylcellulose) such that a conductive gel of appropriate viscosity is created. Other gelling agents, such as PVP (polyvinylpyrrolidone), PEO (polyethyleneoxide), or PVA (polyvinylalcohol) can also be used. Successful gels have been formulated from a HPMC powder at 2% w/w contained in an absorbent scrim.

As packaged, the integrated iontophoresis patch of the invention is designed to contain the therapeutic material to be administered, preferably in the form of a hydrogel absorbed into the absorbent composite pads 124 and contained within the patch as manufactured. Thus, the only operation left to the user may be to open the packaging and apply the patch to an affected area sought to be treated. In this way, subjects can successfully treat themselves by simply positioning the patch on the skin using the adhesive at the desired position.

As indicated, the hydrogel absorbent pads may also be separately stored in common packaging and simply applied to the patch when the package is opened.

One preferred embodiment used as an example herein is dedicated to the administration of donepezil HCl. Donepezil HCl, a cholinestrase inhibitor is indicated for the treatment of mild to moderate Alzheimer's, the seventh-leading cause of death in the United States. Patient compliance with a highly frequent dosage regimen is a limiting factor in cognitive dysfunction. Clinical usefulness of oral dosage forms is also limited by the gastrointestinal side effects caused by activation of the peripheral cholinergic system. As indicated, Donepezil HCl has also been identified as a definite skin irritant considered harmful if in contact with skin by Sequoia Research in its Material Safety Data Sheet (MSDS).

In accordance with the present development, iontophoresis has been successfully used as a technique to achieve the desired therapeutic levels using low cost, disposable, easy to use "active" patches utilizing a low level DC current to propel like charged ions of soluble salts non-invasively across the skin. Donepezil (MW=415.96, pKa=8.9), in its HCl salt form, is positively charged at a pH of 6.0 and therefore would be a desirable candidate for anodal iontophoretic delivery if the negative indication related to skin irritation could be overcome.

While certain embodiments of the invention have been described above in connection with the delivery of Donepezil HCL, as summarized above, the invention is suitable for delivery of a wide variety of active agents. For example, other agents finding use in the treatment of Alzheimer's disease may be delivered via devices of the invention, such as but not limited to: rivastigmine, galantamine, tacrine, amiridine, minaprine, huperzine and huprine.

Another type of active agent of interest that may be present in devices of the invention is an anti-emetic. Specific anti-emetic agents of interest include, but are not limited to: alosetron, azasetron, bemesetron, cilansetron, dolasetron, granisetron, indisetron, itasetron, ondansetron, palonosetron, ramosetron, tropisetron, and zatosetron.

Also of interest are analgesics. Analgesics of interest include, but are not limited to: fentanyl, sufentanil, carfentanhl, lofentanil, alfentanil, hydromorphone, oxycodone, propoxyphene, pentazocine, methadone, tilidine, butorphanol, buprenorphine, levorphanol, codeine, oxymorphone, meperidine, and dihydrocodeinone.

Of course, other types of agents may also be administered using devices of the invention, and the invention is not limited to delivery of the above specific active agents in its broadest sense.

Experiments were conducted to demonstrate that the sacrificial electrodes designed in accordance with the present invention are reliable and skin-safe for prolonged delivery periods, using donepezil HCl as a model compound. In a first experiment, Example I, current measurements and blood analysis were conducted to verify that the drug was delivered in continuous fashion over the entire application period. In a second experiment, Example II, an evaluation was conducted to determine whether the prolonged delivery device built in accordance with this invention has minimal irritation potential. In a third experiment, Example III, an experiment was conducted to determine whether a prolonged delivery device built in accordance with this invention has minimal skin sensitization potential.

Example I

A wearable electronic drug delivery device was used to demonstrate feasibility of iontophoretic delivery and effect of current on the therapeutic dose of Donepezil HCl delivered in hairless rats, using sacrificial electrodes designed in accordance with this invention.

Experimental Methods

Patches consisting of an Ag anode and Ag/AgCl cathode with 7 volts of power were used. A series transistor was used in each patch to set the current to a desired level. Anode and cathode absorbent pads were imbibed overnight with the drug and saline formulation respectively, and used the next day. The current levels set and the expected dose/day (established from previous in vitro measurements of efficiency) are as follows:

TABLE I

Experimental design showing the treatment groups with the targeted dose

| Group No. | Treatment (current level) | No. of animals | Target dose level (mg/day) |
|---|---|---|---|
| 1 | IV | 3 | — |
| 2 | Passive (0 mA) | 4 | 0 |
| 3 | 0.13 mA | 4 | 2.5 |
| 4 | 0.26 mA | 4 | 5.0 |
| 5 | 0.39 mA | 4 | 7.5 |

Current was monitored throughout the application period to ensure proper connections. Patches were placed on each animal for 24 hours and blood samples collected till 72 hrs at predetermined time points. Drug was extracted from the plasma samples by protein precipitation and analyzed by RP-HPLC using fluorescence detection at an excitation of 325 nm and emission of 390 nm. Pharmacokinetic analysis was done using WinNonlin.

Results and Discussion

Figure 7:
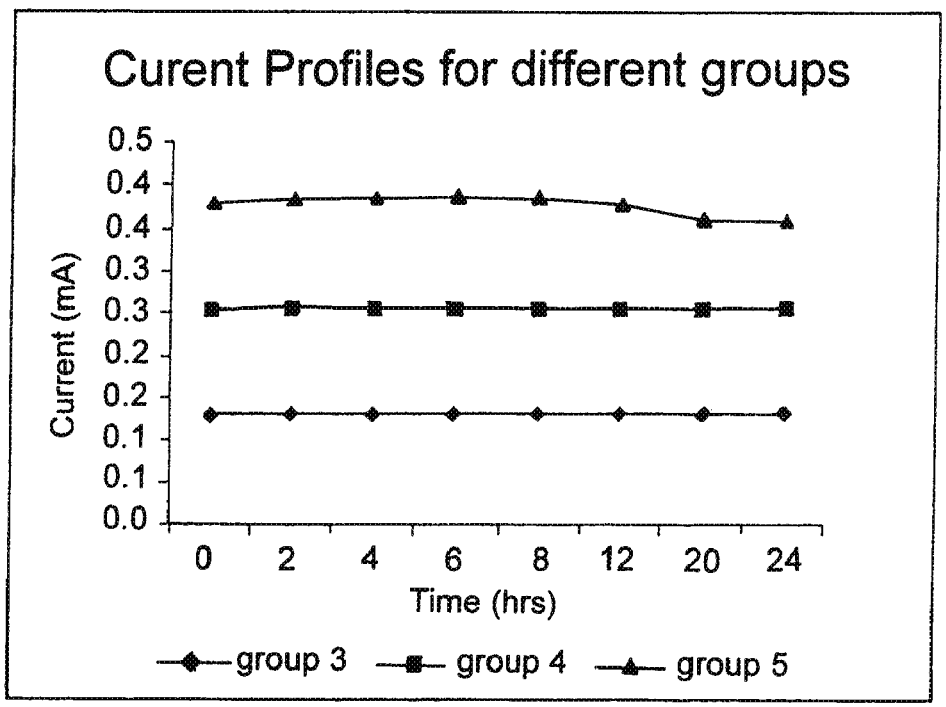
FIG. 7 depicts a graphical representation of current levels of several groups of hairless rats during a 24-hour iontophoresis experiment.

A constant current level was maintained in all the groups indicating the reliability of the electrodes (FIG. 7).

Figure 8:
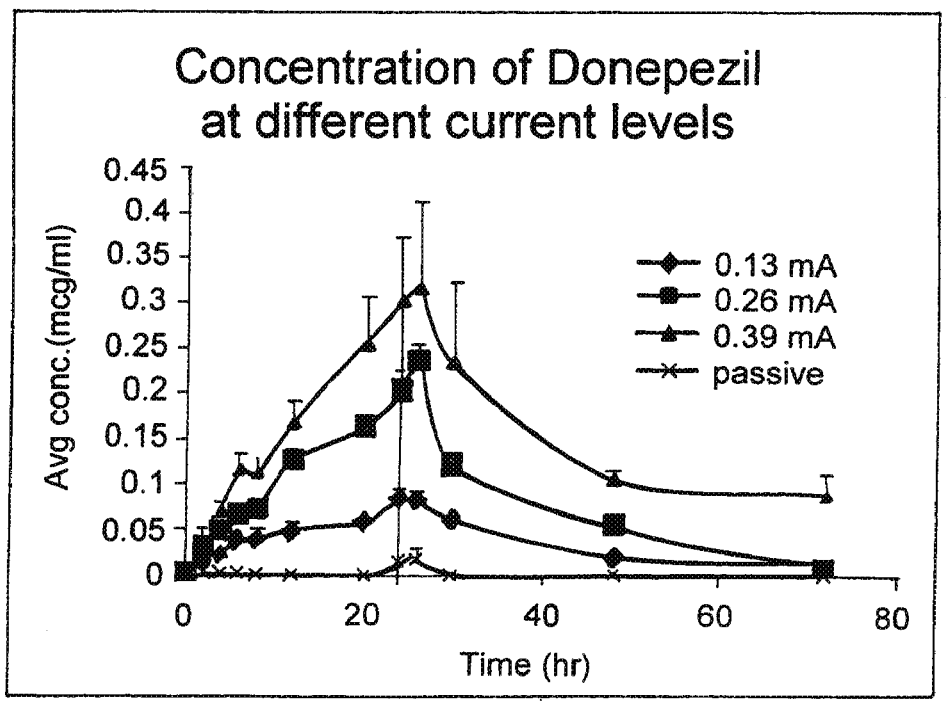
FIG. 8 depicts the relation between agent deliveries and current levels compared with passive administration for donepezil HCl.

A significant increase in the amount of donepezil delivered across hairless rat skin was seen with increasing current levels in comparison with the passive delivery as seen in FIG. 8.

Figure 9:
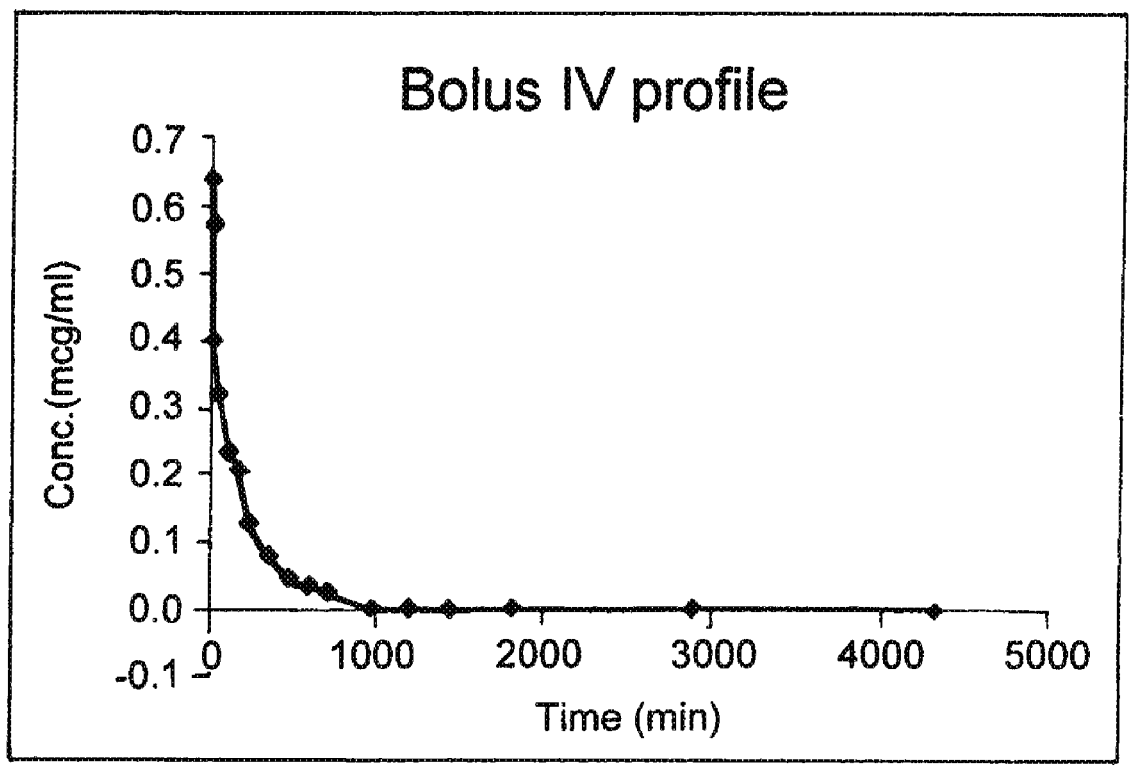
FIG. 9 depicts a bolus profile for donepezil administered by IV.

Clearance values from IV bolus dosing (FIG. 9, Table II) were used to calculate the dose delivered per day (Table III).

TABLE II

IV bolus pharmacokinetic parameters (n = 3)

| Parameter | Units | Value |
|---|---|---|
| Elimination rate const. ($\lambda_z$) | (1/hr) | 0.19 |
| Volume of distribution ($V_z$) | (ml/kg) | 12766.66 |
| Clearance | (ml/hr/kg) | 2285.733 |
| $AUC_{0-\alpha}$ | (hr*ug/ml) | 1.076667 |

TABLE III

Dose delivered for different groups

| Group | Dose delivered ± SD (mg/day) | Desired level (mg/day) |
|---|---|---|
| 2 (passive) | 0 | 0 |
| 3 (0.13 mA) | 2.55 ± 0.75 | 2.5 |
| 4 (0.26 mA) | 5.83 ± 0.37 | 5.0 |
| 5 (0.39 mA) | 8.75 ± 2.83 | 7.5 |

Conclusion

Donepezil HCl was successfully delivered iontophoretically over a prolonged period without interruption or evidence of premature failure. Transdermal iontophoretic delivery also achieved the desired therapeutic levels of 2.5, 5.0 and 7.5 mg per day.

Example II

Primary Skin Irritation Test Results

PURPOSE: This test was designed to determine the dermal irritation potential of the test iontophoretic patch on the shaved skin of the rabbit, as required by certain regulations for medical device biocompatibility.

TEST SAMPLE PREPARATION: The test articles were prepared by instilling 0.5 mL of gel onto each electrode pad of the iontophoretic device. The gel was spread uniformly on the pad and allowed to absorb for approximately 24 hours.

EXPERIMENTAL METHODS SUMMARY: Prior to application, the gel pads were placed on the patches labeled drug and the saline gel pads were placed on the patches labeled saline. In addition, negative control patches were prepared by placing dry pads onto adhesive patches. The prepared patches were applied to the shaved dorsal skin of three (3) adult albino rabbits, two (2) test articles ("drug" and "saline") and one (1) negative control patch on each side of the paravertebral skin. The trunk of each animal was wrapped with an elastic bandage secured with hypoallergenic tape for a minimum 6 hour exposure. Observations for skin irritation were conducted at 60±6 minutes after unwrapping, and at 24±2, 48±2, and 72±2 hours. The tissue reactions were rated for gross evidence of erythema and edema.

The sum of the erythema and edema scores for the test article and control sites were calculated for only the 24, 48 and 72 hour observation periods for each rabbit. The total scores were divided by 6 (2 observation sites×3 observation periods) to determine the Primary Irritation Score observation average. The Primary Irritation Score for the test sites of each rabbit were then totaled and subtracted from the total of the control Primary Irritation Score. This value was divided by the total number of animals to yield the Primary Irritation Index. A negligible, slight, moderate or severe response of the test article was categorized based on the Primary Irritation Index (PII) Table IV.

TABLE IV

PRIMARY IRRITATION RESPONSE CATEGORIES IN THE RABBIT

| RESPONSE CATEGORY | COMPARATIVE MEAN SCORE (PII) |
|---|---|
| Negligible | 0 to 0.4 |
| Slight | 0.5 to 1.9 |
| Moderate | 2 to 4.9 |
| Severe | 5 to 8 |

Note - The Primary Irritation Index (PII) is determined by adding the Primary Irritation Score for each animal and dividing the total score by the number of animals.

RESULTS: See Table V. Primary Irritation Index (PII)=0

CONCLUSION: The test article is considered a non-irritant.

TABLE V

TEST AND CONTROL TOTALS
CALCULATION OF THE PRIMARY IRRITATION SCORE FOR EACH RABBIT

| | 60 MINUTES | | 24 HOUR | | 48 HOUR | | 72 HOUR | | SUM OF OBSERVATIONS | OBSERVATION AVERAGE |
|---|---|---|---|---|---|---|---|---|---|---|
| | LEFT | RIGHT | LEFT | RIGHT | LEFT | RIGHT | LEFT | RIGHT | | |
| RABBIT #3951 | | | | | | | | | | |
| Total TEST (Drug Scores) | 0 | 0 | 0 | 0 | 0 | 0 | 0 | 0 | 0 | 0/6 |
| Total TEST (Saline) Scores | 0 | 0 | 0 | 0 | 0 | 0 | 0 | 0 | 0 | 0/6 |
| Total CONTROL Scores | 0 | 0 | 1 | 0 | 0 | 0 | 0 | 0 | 1 | 1/6 |
| Primary Irritation Score Test Observation Average (−) Control Observation Average | | | | | | | | | | 0* |
| RABBIT #3952 | | | | | | | | | | |
| Total TEST (Drug Scores) | 0 | 0 | 0 | 0 | 0 | 0 | 0 | 0 | 0 | 0/6 |
| Total TEST (Saline) Scores | 0 | 0 | 0 | 0 | 0 | 0 | 0 | 0 | 0 | 0/6 |
| Total CONTROL Scores | 0 | 0 | 0 | 0 | 0 | 0 | 0 | 0 | 0 | 0/6 |
| Primary Irritation Score Test Observation Average (−) Control Observation Average | | | | | | | | | | 0* |
| RABBIT #3953 | | | | | | | | | | |
| Total TEST (Drug Scores) | 0 | 0 | 0 | 0 | 0 | 0 | 0 | 0 | 0 | 0/6 |
| Total TEST (Saline) Scores | 0 | 0 | 0 | 0 | 0 | 0 | 0 | 0 | 0 | 0/6 |
| Total CONTROL Scores | 0 | 0 | 0 | 0 | 0 | 0 | 0 | 0 | 0 | 0/6 |
| Primary Irritation Score Test Observation Average (−) Control Observation Average | | | | | | | | | | 0* |

TABLE V-continued

TEST AND CONTROL TOTALS
CALCULATION OF THE PRIMARY IRRITATION SCORE FOR EACH RABBIT

| RABBIT # | PRIMARY IRRITATION SCORES | IRRITATION RESPONSE CATEGORY |
|---|---|---|
| 3951 | 0 | 0 to 0.4 - - - |
| 3952 | 0 | Negligible |
| 3953 | 0 | |
| Total | 0 | |
| Primary Irritation Index (PII) Total/3 | 0 | |

*Negative value is reported as zero.

TECHNICAL REFERENCES

16 CFR, Part 1500.41, Method of Testing Primary Irritant Substances, 1-1 97.

ISO 10993-10: 2002 Standard, "Biological Evaluation of Medical Devices, Part 10-Tests for Irritation and Sensitization" pp. 6-10, 21.

Marzulli, F. N., Maibach, H. I., Dermatotoxicology 4th Edition, pp. 201-208, Hemisphere Publishing Corp. New York, N.Y., 1991.

U.S. EPA—Office of Prevention, Pesticides and Toxic Substances (OPPTS), Health Effects Test Guidelines, OPPTS 870.1200 Acute Dermal Toxicity.

Example III

Repeated Patch Dermal Sensitization Test

Buehler Method Modified for Medical Devices

PURPOSE: This test was designed to evaluate the allergenic potential or sensitizing capacity of the iontophoretic test article. This test was used as a procedure for the screening of contact allergens in guinea pigs and extrapolating the results to humans, but does not establish the actual risk of sensitization in humans.

TEST SAMPLE PREPARATION: The test article consisted of an iontophoretic device having electrodes of this invention, with white adsorbant pads having clear drug and saline gels.

EXPERIMENTAL METHODS SUMMARY: Ten test guinea pigs were patched with the test article and five guinea pigs were patched with a control blank. The bandages and patches were removed after six (6) hours of exposure. After a 24 hour rest period, each site was observed on each animal for erythema and edema. This procedure was repeated once per week for three weeks for a total of three applications. Following a two week rest period, the animals were topically patched with the appropriate test article on the nine test animals and the control blank on the control animals. The patches were removed after 6 hours of exposure. The dermal patch sites were observed for erythema and edema 24 and 48 hours after patch removal. Each animal was assessed for a sensitization response based upon the dermal scores. The test results were based upon incidence and severity of the sensitization reaction.

Results for the study are summarized in Tables VI-IX.

CONCLUSION: The test article is considered a non-sensitizer.

TABLE VI

DERMAL CHALLENGE SUMMARY

| MEASURED CRITERIA | 24 HOURS | 48 HOURS |
|---|---|---|
| Test Group Challenge Score Totals | 0 | 0 |
| Severity (Total/10) | 0/10 | 0/10 |
| Incidence % | 0% | 0% |
| Control Group Challenge Score Totals | 0 | 0 |
| Severity (Total/5) | 0/5 | 0/5 |
| Incidence % | 0% | 0% |

TABLE VII

INDUCTION DERMAL OBSERVATIONS 24 HOURS AFTER UNWRAPPING

| | PATCH 1 | | PATCH 2 | | PATCH 3 | |
|---|---|---|---|---|---|---|
| | | | TEST GROUP | | | |
| ANIMAL # | NS | Drug[a] | NS | Drug[a] | NS | Drug[a] |
| 39801 | 0 | 0 | 0 | 0 | 0 | 0 |
| 39802 | 0 | 0 | 0 | 0 | 0 | 0 |
| 39803 | 0 | 0 | 0 | 0 | 0 | 0 |
| 39804 | 0 | 0 | 0 | 0 | 0 | 0 |
| 39805 | 0 | 0 | 0 | 0 | 0 | 0 |
| 39806 | 0 | 0 | 0 | 0 | 0 | 0 |
| 39807 | 0 | 0 | 0 | 0 | 0 | 0 |
| 39808 | 0 | 0 | 0 | 0 | 0 | 0 |
| 39809 | 0 | 0 | 0 | 0 | 0 | 0 |
| 39810 | 0 | 0 | 0 | 0 | 0 | 0 |
| NEGATIVE CONTROL GROUP | | | | | | |
| | NS | Drug[b] | NS | Drug[b] | NS | Drug[b] |
| 39811 | 0 | 0 | 0 | 0 | 0 | 0 |
| 39812 | 0 | 0 | 0 | 0 | 0 | 0 |
| 39813 | 0 | 0 | 0 | 0 | 0 | 0 |
| 39814 | 0 | 0 | 0 | 0 | 0 | 0 |
| 39815 | 0 | 0 | 0 | 0 | 0 | 0 |

[a] = Drug patch with Sponsor supplied test article
[b] = Drug patch with Normal Saline only (Sponsor supplied)

TABLE VIII

CHALLENGE DERMAL OBSERVATIONS
(24 HOURS POST UNWRAPPING)

| | 24 HOURS | | 48 HOURS | |
|---|---|---|---|---|
| | Test Group Patches | | | |
| ANIMAL # | NS | Drug[a] | NS | Drug[a] |
| 39801 | 0 | 0 | 0 | 0 |
| 39802 | 0 | 0 | 0 | 0 |
| 39803 | 0 | 0 | 0 | 0 |
| 39804 | 0 | 0 | 0 | 0 |

TABLE VIII-continued

CHALLENGE DERMAL OBSERVATIONS
(24 HOURS POST UNWRAPPING)

| 39805 | 0 | 0 | 0 | 0 |
|---|---|---|---|---|
| 39806 | 0 | 0 | 0 | 0 |
| 39807 | 0 | 0 | 0 | 0 |
| 39808* | — | — | — | — |
| 39809 | 0 | 0 | 0 | 0 |
| 39810 | 0 | 0 | 0 | 0 |
| TOTAL OF SCORES | 0 | 0 | 0 | 0 |
| SEVERITY (TOTAL/10) | 0/10 | 0/10 | 0/10 | 0/10 |
| INCIDENCE % | 0% | 0% | 0% | 0% |

| | NEGATIVE CONTROL GROUP | | | |
|---|---|---|---|---|
| ANIMAL # | NS | Drug[b] | NS | Drug[b] |
| 39811 | 0 | 0 | 0 | 0 |
| 39812 | 0 | 0 | 0 | 0 |
| 39813 | 0 | 0 | 0 | 0 |
| 39814 | 0 | 0 | 0 | 0 |
| 39815 | 0 | 0 | 0 | 0 |

*Animal found dead on day 19, considered to be unrelated to the test article
[a] = Drug patch with Sponsor supplied test
[b] = Drug patch with Normal Saline only (Sponsor supplied)

TABLE IX

POSITIVE CONTROLS (RUN Mar. 28, 2007)

| ANIMAL # | 24 HOURS SCORE | 48 HOURS SCORE |
|---|---|---|
| TEST GROUP | | |
| 35464 | 2 | 1 |
| 35465 | 1 | 1 |
| 35466 | 2 | 1 |
| 35467 | 2 | 2 |
| 35468 | 2 | 2 |
| 35469 | 2 | 2 |
| 35470 | 2 | 2 |
| 35471 | 1 | 1 |
| 35472 | 2 | 1 |
| 35473 | 2 | 2 |
| TOTAL OF SCORES | 18 | 15 |
| SEVERITY (TOTAL/10) | 18/10 | 15/10 |
| INCIDENCE % | 100% | 100% |
| NEGATIVE CONTROL GROUP | | |
| 35474 | 0 | 0 |
| 35475 | 0 | 0 |
| 35476 | 0 | 0 |
| 35477 | 0 | 0 |
| 35478 | 0 | 0 |
| TOTAL OF SCORES | 0 | 0 |
| SEVERITY (TOTAL/5) | 0/5 | 0/5 |
| Incidence % | 0% | 0% |

TECHNICAL REFERENCES

Dermatotoxicology, Marzulli, F. N. and Maibach, H. I., editors, 4th edition, 1991, pp 381-3385, Hemisphere Publishing Corporation, New York.
ISO 10993-10: 1995 Standard, "Biological Evaluation of Medical Devices, Part 10-Tests for Irritation and Sensitization" pp. 13-15.
Principles and Methods of Toxicology, Wallace Hayes, A., editor, 3rd edition, 1994. Dermatotoxicology Chapter 21, pp. 777, Ravin Press, New York.
Ritz H. L. and Buehler E. V. (1980). Procedure for Conducting the Guinea Pig Assay. Current Concepts in Dermatology, Drill V. A. and Lazar P. (eds), Academic Press, New York, N.Y., pp 25-40.
U.S. EPA—Office of Prevention, Pesticides and Toxic Substances (OPPTS), Health Effects Test Guidelines, OPPTS 870.2600 Skin Sensitization

What is claimed is:

1. A wearable iontophoresis device for the prolonged delivery of a positively charged pharmaceutical species from a salt formulation comprising:
    (a) a readily oxidizable metal-based sacrificial anode in the form of a generally planar layer having a connecting neck area that has a width that is generally 5% or more of the maximum electrode width dimension such that said sacrificial anode will remain connected for the desired operating life of the sacrificial anode;
    wherein the sacrificial anode is configured to have a minimum operating life of at least 6 hours under skin-safe conditions and is entirely consumed during the prolonged operation of the sacrificial anode; and
    (b) a drug delivery gel pad in electrical contact with said anode for accommodating a gel containing a positively charged pharmaceutical species in salt form formulated for transdermal delivery.

2. A device as in claim 1 wherein said width of said neck area is $\geq 10\%$ of said maximum anode width.

3. A device as in claim 1 wherein said salt is a hydrochloride.

4. A device as in claim 3 wherein said hydrochloride is donepezil HCl.

5. A device as in claim 1 wherein said readily oxidizable metal is silver.

6. A device as in claim 3 wherein said readily oxidizable metal is silver.

7. A device as in claim 4 wherein said readily oxidizable metal is silver.

8. A device as in claim 1 wherein said anode has a surface having a rough texture in contact with said drug delivery pad thereby increasing the contact area therebetween.

9. A device as in claim 5 wherein said anode has a surface having a rough texture in contact with said drug delivery pad thereby increasing the contact area therebetween.

10. A device as in claim 1 wherein said anode includes a plurality of neck connecting segments.

11. A device as in claim 7 wherein said anode includes a plurality of neck connecting segments.

12. A device as in claim 1 comprising circuit components to control output current such that said drug delivery is made using a current density $\leq 100$ $\mu$A l cm$^2$.

13. A device as in claim 1 wherein said anode has a maximum life of 7 days or more.

14. A device as in claim 12 wherein said anode has a maximum life of 7 days or more.

15. A device as in claim 1 wherein said anode is formed as a layer on said drug delivery pad.

16. A device as in claim 1 wherein said positively charged species is donepezil.

17. A device as in claim 1 including a readily reducible cathode in series with said anode.

18. A device as in claim 17 that operates at a stable pH at both electrodes.

19. A device as in claim 4 wherein the concentration of said donepezil HCl is generally 10% or less and is contained in an aqueous hydrogel.

20. A sacrificial anode for an iontophoresis device for long term operation comprising:
(a) an amount of readily oxidizable metal forming a continuous layer on a drug delivery gel pad substrate, wherein the amount is entirely consumed during the prolonged operation of the sacrificial anode;
(b) a conductive connecting segment connecting said continuous layer in an iontophoresis circuit, said connecting segment having a width generally 5% or more of the maximum width of said sacrificial anode such that said anode will remain connected for the designed operating life of the anode; and
(c) wherein said drug delivery gel pad has a rough surface.

21. A sacrificial anode as in claim 20 wherein the thickness of said silver is from about 5 microns to about 50 microns.

22. A sacrificial anode as in claim 20 wherein said width of said connecting segment is $\geq$10% of said maximum anode width.

23. A sacrificial anode as in claim 21 wherein said width of said connecting segment is $\geq$10% of said maximum anode width.

24. An iontophoresis device for the prolonged delivery of a positively charged species from an HCl salt formulation comprising:
(a) a silver-based sacrificial anode in the form of a generally planar layer having a neck area of a width that is generally 5% or more of the maximum electrode width dimension such that said sacrificial anode will remain connected for the designed operating life of the sacrificial anode and a compatible readily reduced cathode, wherein the silver-based sacrificial anode is configured to have a minimum operating life of at least 6 hours and is entirely consumed during the prolonged operation of the sacrificial anode;
(b) an absorbent drug delivery pad in electrical contact with said anode for receiving and absorbing a gel containing a positively charged species in hydrochloride salt form for delivery; and
(c) circuit components to control output current such that drug delivery is made using a current generally $\leq$100 $\mu$A/cm$^2$.

25. A device as in claim 24 wherein said width of said neck area is 10% of said maximum anode width.

26. A device as in claim 24 wherein said hydrochloride is donepezil HCl.

27. A device as in claim 24 wherein said silver-based anode has a rough surface texture and forms a layer on said drug pad.

28. A method of fabricating a sacrificial anode for use in drug delivery, the method comprising:
silk screening an amount of readily oxidized metal in a manner sufficient to form a layer on an absorbent drug delivery gel pad for containing an amount of a conductive hydrogel including a pharmaceutical species, wherein said sacrificial anode is provided with a connecting neck area such that it will remain connected in a corresponding circuit for the designed operating life of the anode.

29. A method as in claim 28 wherein the sacrificial anode is fabricated with a neck area generally $\geq$5% of the greatest width of the anode.

30. A method as in claim 28 wherein the readily oxidized metal is silver.

31. A method as in claim 29 wherein the readily oxidized metal is silver.

32. A method as in claim 28 wherein the surface of the gel pad is rough.

33. A method as in claim 28 including formulating an amount of a salt of said pharmaceutical species in said hydrogel and causing said hydrogel to be absorbed into said gel pad.

34. A method as in claim 33 wherein said salt is a hydrochloride.

35. A method as in claim 33 wherein said salt is donepezil HCl.

36. A method of transdermally administering a positively charged pharmaceutical substance to a subject for a prolonged period in a skin-safe manner comprising:
(a) providing a wearable iontophoresis device as in claim 1 in which the positively charged species is added in gel form; and
(b) applying said iontophoresis device to the skin of a subject for a period of from 6 hours to 7 days.

37. A method as in claim 36 wherein said pharmaceutical species is selected from the group consisting of analgesics, anti-emetics, agents useful in treating Alzheimer's disease and substances that are normally skin irritants.

38. A method as in claim 37 wherein said species is donepezil.

39. A device as in claim 1 wherein said pharmaceutical species is selected from the group consisting of analgesics, anti-emetics, agents useful in treating Alzheimer's disease and substances that are normally skin irritants.

40. A device as in claim 24 wherein said pharmaceutical species is selected from the group consisting of analgesics, anti-emetics and substances that are normally skin irritants.

41. A device as in claim 28 wherein said pharmaceutical species is selected from the group consisting of analgesics, anti-emetics and substances that are normally-skin irritants.

42. A device as in claim 24 wherein said circuit components comprise a silver chloride cathode.

43. A device as in claim 1, wherein said device further includes an integrated source of electric power.

44. A device as in claim 20, wherein said device further includes an integrated source of electric power.

45. A device as in claim 24, wherein said device further includes an integrated source of electric power.

46. A device as in claim 28, wherein said device further includes an integrated source of electric power.

47. A wearable iontophoresis device for the prolonged delivery of a positively charged pharmaceutical species from a salt formulation comprising:
(a) a readily oxidizable metal-based sacrificial anode in the form of a generally planar layer having a connecting neck area that has a width that is generally 5% or more of the maximum electrode width dimension such that the sacrificial anode will remain connected for the desired operating life of the anode;
(b) wherein the sacrificial anode is configured to have a minimum operating life of at least 6 hours under skin-safe conditions;
(c) a drug delivery gel pad in electrical contact with said anode for accommodating a gel containing a positively charged pharmaceutical species in salt form formulated for transdermal delivery; and
(d) an integrated source of electric power.

* * * * *